United States Patent
Shimizu et al.

(10) Patent No.: US 11,104,655 B2
(45) Date of Patent: Aug. 31, 2021

(54) METHOD FOR PRODUCING CYCLIC ETHER

(71) Applicants: Ryosuke Shimizu, Kamisu (JP); Takahiro Hosono, Kamisu (JP); Ichihiro Aratani, Tsukuba (JP); Ryo Kouchi, Kamisu (JP)

(72) Inventors: Ryosuke Shimizu, Kamisu (JP); Takahiro Hosono, Kamisu (JP); Ichihiro Aratani, Tsukuba (JP); Ryo Kouchi, Kamisu (JP)

(73) Assignee: KURARAY CO., LTD., Kurashiki (JP)

( * ) Notice: Subject to any disclaimer, the term of this patent is extended or adjusted under 35 U.S.C. 154(b) by 0 days.

(21) Appl. No.: 16/770,405

(22) PCT Filed: Dec. 4, 2018

(86) PCT No.: PCT/JP2018/044457
§ 371 (c)(1),
(2) Date: Jun. 5, 2020

(87) PCT Pub. No.: WO2019/111865
PCT Pub. Date: Jun. 13, 2019

(65) Prior Publication Data
US 2020/0290983 A1 Sep. 17, 2020

(30) Foreign Application Priority Data
Dec. 7, 2017 (JP) .............................. JP2017-235222

(51) Int. Cl.
*C07D 307/08* (2006.01)
*B01J 23/44* (2006.01)
*C07D 309/04* (2006.01)

(52) U.S. Cl.
CPC ............ *C07D 307/08* (2013.01); *B01J 23/44* (2013.01); *C07D 309/04* (2013.01)

(58) Field of Classification Search
CPC ................................................. C07D 307/08

USPC ........................................................ 549/509
See application file for complete search history.

(56) References Cited

U.S. PATENT DOCUMENTS

| | | |
|---|---|---|
| 6,239,295 B1 | 5/2001 | Iwasaki |
| 6,593,481 B1 | 7/2003 | Manzer |
| 2004/0122241 A1 | 6/2004 | Beavers et al. |

FOREIGN PATENT DOCUMENTS

| | | |
|---|---|---|
| DE | 10 2006 028 618 A1 | 1/2007 |
| JP | 2001-226366 A | 8/2001 |
| JP | 2004-203856 A | 7/2004 |
| JP | 2005-511624 A | 4/2005 |
| JP | 2006/188492 A | 7/2006 |
| WO | WO 2014/188843 A1 | 11/2014 |

OTHER PUBLICATIONS

Li, Yuchui, et al., "Lewis Acid Promoted Ruthenium (II)—Catalyzed Etherifications by Selective Hydrogenation of Carboxylic Acids/Esters," Angewandte Chemie, International Edition, vol. 54, No. 17, 2015, pp. 5196-5200.
Schniepp, L.E. et al., "The Preparation of Acetopropyl Alcohol and 1,4-Pentanediol From Methylfuran," Journal of the American Chemical Society, vol. 69, 1947, pp. 672-674.
International Search Report dated Mar. 5, 2019 in PCT/JP2018/044457 filed on Dec. 4, 2018, 2 pages.
European Search Report as received in the corresponding EP18886780.8-1110/3722287 dated May 7, 2021, 8 pages.
Anne Boussonmete, et al, "Radical Cyclizaton α-Bromo Aluminum Acetals omo Alkenes and Alkynes (Radic[A1] Process): A Simple Keces to γ-Lactols and 4-Methylene-γ-Lacsols", Chem. Eur. J. 2011, 17, 5613-5627, 15 pages.

*Primary Examiner* — Taofiq A Solola
(74) *Attorney, Agent, or Firm* — Oblon, McClelland, Maier & Neustadt, L.L.P.

(57) ABSTRACT

A method for producing a cyclic ether represented by formula (2) includes reacting a 2-hydroxy cyclic ether, represented by formula (1), with hydrogen in the presence of a catalyst.

13 Claims, No Drawings

METHOD FOR PRODUCING CYCLIC ETHER

TECHNICAL FIELD

The present invention relates to a method for producing a cyclic ether.

BACKGROUND ART

A method for producing a cyclic ether is conventionally known which involves reacting 2-alkoxytetrahydropyran with hydrogen in the presence of an acid and a catalyst to synthesize tetrahydropyran (PTL 1). However, 2-alkoxytetrahydropyran for use in this method is not industrially available at low cost. Further, this method has room for improvement in the yield.

Further, a method for synthesizing a cyclic ether from a hydroxy cyclic ether is known which involves dehydrating 3-hydroxy-3-methyltetrahydrofuran in the presence of an acidic material to obtain 3-methyldihydrofuran, and then synthesizing 3-methyltetrahydrofuran in the presence of a hydrogenation catalyst (PTL 2). However, this method, which uses the two-step reaction, is undesirable from an industrial point of view. In addition, this method has room for improvement in the yield.

Further, a method is known which synthesizes tetrahydrofuran by reacting 3,4-dihydroxytetrahydrofuran with hydrogen in the presence of a catalyst (PTL 3). However, this method cannot achieve a high yield.

CITATION LIST

Patent Literature

PTL 1: JP 2006-188492 A
PTL 2: JP 2001-226366 A
PTL 3: WO 2014/188843

SUMMARY OF INVENTION

Technical Problem

In view of the above problems in the conventional known methods for the production of a cyclic ether, it is an object of the present invention to provide a method which uses a readily available compound and can produce a cyclic ether with a high yield in a simple manner under mild conditions.

Solution to Problem

The present inventors, through intensive studies, have found that the above problems can be solved by reacting a particular 2-hydroxy cyclic ether with hydrogen in the presence of a catalyst. The present invention has been achieved based on this finding.

The present invention relates to the below-described methods [1] to [8].

A method for producing a cyclic ether represented by the following formula (2) (hereinafter also referred to as the "cyclic ether (2)"), including reacting a 2-hydroxy cyclic ether, represented by the following formula (1) (hereinafter also referred to as the "2-hydroxy cyclic ether (1)"), with hydrogen in the presence of a catalyst:

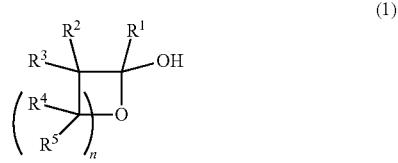

wherein n is an integer in the range of 1 to 7, and $R^1$ to $R^5$ each independently represent a hydrogen atom, an aliphatic hydrocarbon group having 1 to 4 carbon atoms or an aromatic hydrocarbon group having 6 to 12 carbon atoms, and when $R^4$ and $R^5$ exist plurally, they may differ from each other;

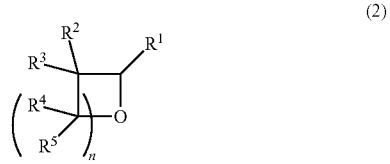

wherein the symbols have the above-defined meanings.

[2] The production method as described in [1], wherein the reaction is carried out under the condition that the pH of the reaction mixture falls within the range of 3 to 7.

[3] The production method as described in [1], wherein at least one acid selected from the group consisting of acetic acid, phosphoric acid, sulfuric acid, hydrochloric acid, nitric acid, a heteropoly acid and a peracid, or a salt thereof is allowed to exist and react in the reaction mixture in an amount of 0.001 to 10% by mass based on the total mass of the reaction mixture.

[4] The production method as described in any one of [1] to [3], wherein the catalyst includes an element from groups 8 to 10 of the periodic table.

[5] The production method as described in [4], wherein the element from groups 8 to 10 of the periodic table is at least one element selected from the group consisting of nickel, ruthenium, rhodium, palladium and platinum.

[6] The method as described in [4] or [5], wherein the catalyst is a supported catalyst.

[7] The production method as described in any one of [1] to [6], wherein $R^1$ is a hydrogen atom.

[8] The production method as described in any one of [1] to [7], wherein n is 2 or 3.

Advantageous Effects of Invention

According to the production method of the present invention, a cyclin ether can be produced with a high yield in a simple manner under mild conditions using a readily available compound.

DESCRIPTION OF EMBODIMENTS

Embodiments of the present invention will now be descried in detail.

The present invention is a method for producing the cyclic ether (2), which includes reacting the 2-hydroxy cyclic ether (1) with hydrogen in the presence of a catalyst.

In the 2-hydroxy cyclic ether (1), n is an integer in the range of 1 to 7. n is preferably an integer in the range of 1 to 5, more preferably an integer in the range of 1 to 3, and even more preferably 2 or 3.

In the 2-hydroxy cyclic ether (1), $R^1$ to $R^5$ each independently represent a hydrogen atom, an aliphatic hydrocarbon group having 1 to 4 carbon atoms or an aromatic hydrocarbon group having 6 to 12 carbon atoms. When $R^4$ and $R^5$ exist plurally, they may differ from each other. Thus, when there exist two $R^4$s, they may be the same, or different from each other; for example, one may be a hydrogen atom, and the other may be a methyl group. Preferably, $R^1$ to $R^5$ each independently represent a hydrogen atom or an aliphatic hydrocarbon group having 1 to 3 carbon atoms, more preferably a hydrogen atom or a methyl group. Even more preferably, $R^1$ to $R^5$ are all hydrogen atoms, or one of $R^1$ to $R^5$ (when $R^4$ and $R^5$ exist plurally, one of all the existing Rs) is a methyl group and the other Rs are all hydrogen atoms. $R^1$ is particularly preferably a hydrogen atom.

The 2-hydroxy cyclic ether (1) is readily available. The compound can be produced, for example, by a method as described in Journal of Molecular Catalysis, Vol. 423, p. 41 (2016), which involves reacting a corresponding unsaturated alcohol (e.g. allyl alcohol) with a mixed gas of carbon monoxide and hydrogen in the presence of a rhodium catalyst.

There is no particular limitation on hydrogen for use in the production method of the present invention; for example, both electrolytic hydrogen and petroleum-derived hydrogen can be used. As used herein, electrolytic hydrogen refers to hydrogen produced by electrolysis of water, and petroleum-derived hydrogen refers to hydrogen obtained by cracking of naphtha. Hydrogen, when used, may be diluted with an inert gas such as nitrogen or argon.

There is no particular limitation on a catalyst for use in the present invention as long as it is capable of hydrogenating the 2-hydroxy cyclic ether (1); however, it is preferred to use a catalyst including an element from groups 8 to 10 of the periodic table.

Specific examples of the element from groups 8 to 10 of the periodic table include cobalt, nickel, ruthenium, rhodium, iridium, palladium and platinum. Among these elements, at least one element selected from the group consisting of nickel, ruthenium, rhodium, palladium and platinum is preferred, and palladium is more preferred.

From the viewpoint of the surface area of a catalyst, it is preferred that a catalyst for use in the present invention be a catalyst supported on a carrier (supported catalyst). Examples of the carrier include activated carbon, silica, alumina, titania and zeolite.

Specific examples of the supported catalyst include palladium-supported activated carbon, platinum-supported activated carbon, palladium-supported silica, palladium-supported alumina and palladium-supported titania.

The amount of the supported element in the supported catalyst is preferably 0.01 to 20% by mass, more preferably 0.1 to 10% by mass, even more preferably 0.5 to 5% by mass based on the total mass of the catalyst. The use of the supported element in an amount of not less than 0.01% by mass can reduce the use of the supported catalyst and can prevent adsorption of the product onto the catalyst. On the other hand, the use of the supported element in an amount of not more than 20% by mass can reduce the use of the element while achieving a sufficiently high yield.

There is no particular limitation on a method for preparing a catalyst for use in the present invention. Examples of the method includes preparing a solution of a nitrate, a chloride, or the like of a catalyst-constituting element, such as the above-described element from groups 8 to 10 of the periodic table, dissolved or suspended e.g. in water or an organic solvent, impregnating a catalyst carrier with the solution, and then reducing the element into its zero-valence state by wet reduction using, for example, hydrazine or by dry reduction using, for example, hydrogen. In this method, all the supported elements need not be in their zero-valence state.

In the production method of the present invention, the catalyst is preferably used in an amount of 0.0001 to 10% by mass, more preferably 0.001 to 5% by mass, even more preferably 0.01 to 3% by mass base on the mass of the 2-hydroxy cyclic ether (1). The use of the catalyst in an amount of not less than 0.0001% by mass can achieve a sufficiently high reactivity. On the other hand, the use of the catalyst in an amount of not more than 10% by mass can reduce the use of the catalyst while achieving a sufficiently high reaction rate.

In the production method of the present invention, the reaction is preferably carried out under the condition that the pH of the reaction mixture falls within the range of 3 to 7, more preferably in the range of 3 to 6, and even more preferably in the range of 4 to 6. The above reaction mixture means the reaction mixture upon a reaction (typically a hydrogenation reaction). When the pH of the system immediately before the introduction of hydrogen is measured, the measured value can be regarded as the pH of the above reaction mixture.

The 2-hydroxy cyclic ether (1) as a raw material is an unstable hemiacetal. Nevertheless, when it is allowed to react under the condition that the pH of the reaction mixture is not less than 3, a side reaction of the raw material or an intermediate is inhibited, resulting in an increased yield. On the other hand, a sufficiently high reaction rate can be achieved by making the pH of the reaction mixture not more than 7.

The pH can be measured using a commercially available pH meter (e.g. pH METER D-12 manufactured by HORIBA Ltd.). Alternatively, the pH may be measured more simply by using commercially available pH test paper (e.g. pH test paper WR 1.0-14.0 manufactured by Toyo Roshi).

In the production method of the present invention, an acidic material is preferably present in the reaction mixture during the reaction.

Examples of the acidic material include inorganic acids such as hydrochloric acid, sulfuric acid, phosphoric acid, polyphosphoric acid, sodium hydrogensulfate, potassium hydrogensulfate, potassium dlihydrogen phosphate, sodium hydrogen sulfite, and potassium hydrogen sulfite; sulfonic acids such as methanesulfonic acid, benzenesulfonic acid, and toluenesulfonic acid; carboxylic acids such as acetic acid, propionic acid, benzoic acid, and terephthalic acid; heteropoly acids such as phosphotungstic acid, phosphomolibdic acid, silicotungstic acid, and silicomolibdic acid; solid acids such as silica, alumina, silica-alumina, titania, silica-titania, niobium oxide, and activated earth; acidic ion exchange resins such as a sulfonic acid-type ion exchange resin and a carboxylic acid-type ion exchange resin; a peracid generated by air oxidation of a compound existing in the reaction mixture; and salts thereof.

Among these materials, at least one acid selected from the group consisting of acetic acid, phosphoric acid, sulfuric acid, hydrochloric acid, nitric acid, a heteropoly acid and a peracid, or a salt thereof is preferred.

These acidic materials may be used singly or in a combination of two or more. Such an acidic material may be supported on a carrier so that it can be used like a solid acid.

In the production method of the present invention, the acidic material is preferably used in such an amount as to make the pH of the reaction mixture fall within the range of 3 to 7. The amount of the acidic material may be 0.001 to 10% by mass, and may be 0.1 to 6% by mass based on the total mass of the reaction mixture.

In the present invention, the reaction can be carried out in the presence or absence of a solvent. There is no particular limitation on the solvent as long as it does not adversely affect the reaction. Examples of usable solvents include aliphatic hydrocarbons such as hexane, heptane, octane, nonane, decane, and cyclohexane; aromatic hydrocarbons such as benzene, toluene, xylene, and mesitylene; alcohols such as methanol, ethanol, isobutanol, normal butanol, ethylene glycol, and 1,5-pentane diol; ethers such as tetrahydrofuran and tetrahydropyran; and water. In the case of using a solvent, there is no particular limitation of the amount of the solvent. However, it is generally preferred to use a solvent in an amount of 0.01 to 10 times the mass of the 2-hydroxy cyclic ether (1). From the viewpoints of smooth progress of the reaction, volumetric efficiency, economy, etc., a solvent is more preferably used in an amount of 0.1 to 2 times the mass of the 2-hydroxy cyclic ether (1).

In the present invention, the reaction temperature is preferably in the range of 40 to 250° C., more preferably in the range of 60 to 180° C. By performing the reaction at a temperature of not less than 40° C., the reaction can be proceeded smoothly. By performing the reaction at a temperature of not more than 250° C., the production of a high-boiling compound as a by-product can be reduced, and thus the selectivity can be enhanced.

There is no particular limitation on the reaction pressure in the present invention; however, the reaction pressure is preferably 1 kPa to 20 MPa, more preferably 0.2 MPa to 10 MPa. A sufficiently high reaction rate can be achieved by performing the reaction at a pressure of not less than 1 kPa. An equipment investment cost can be reduced by performing the reaction at a pressure of not more than 20 MPa.

EXAMPLES

The following examples illustrate the present invention in greater detail and are not intended to limit the scope of the invention. In the examples, gas chromatography analysis was performed under the following conditions, and a yield was determined by an internal reference method using a calibration curve method.

[Gas Chromatography Analysis Conditions]
Analytical instrument: GC-2014 (manufactured by Shimadzu Corporation). Detector: FID (hydrogen flame ionization detector).
Column used: DB-1 (length 30 m, film thickness 0.25 μm, inner diameter 0.25 mm) (manufactured by Agilent Technologies, Inc.).
Analysis conditions: injection temp. 220° C.; detection temp. 220° C.
Temperature rise conditions: 80° C. (kept for 5 min)→(raise temperature at 5° C./min)→220° C. (kept for 5 min).

Example 1

60 g of 2-hydroxytetrahydrofuran (HF), 1.2 g of 5 mass % palladium/activated carbon powder (E1010/W manufactured by Evonik Industries), and 0.6 g of 85% phosphoric acid were placed and mixed in a 100-mL stainless-steel autoclave having a gas introduction port and a sampling port. The pH of the mixture was measured by using a pH test paper strip, manufactured by Toyo Roshi, and found to be 4. The atmosphere in the reactor was replaced with hydrogen and pressurized to 0.5 MPa, and the temperature in the reactor was raised to 100° C. Subsequently, the hydrogen pressure was raised to 1.8 MPa. The mixture was allowed to react for 7 hours. Hydrogen was added during the reaction so as to keep the pressure at 1.8 MPa. Gas chromatography analysis of the reaction mixture after the reaction revealed that the conversion rate of HF was 100% and the yield of tetrahydrofuran (THF) was 100%.

Example 2

60 g of HF, 1.2 g of 5 mass % palladium/activated carbon powder (E1010/W manufactured by Evonik Industries), and 2.4 g of 85% phosphoric acid were placed and mixed in the same autoclave as that of Example 1. The pH of the mixture was measured by using a pH test paper strip, manufactured by Toyo Roshi, and found to be 3. The atmosphere in the reactor was replaced with hydrogen and pressurized to 0.5 MPa, and the temperature in the reactor was raised to 120° C. Subsequently, the hydrogen pressure was raised to 1.8 MPa. The mixture was allowed to react for 4 hours. Hydrogen was added during the reaction so as to keep the pressure at 1.8 MPa. Gas chromatography analysis of the reaction mixture after the reaction revealed that the conversion rate of HF was 96% and the yield of THF was 94%.

Example 3

60 g of HF, 1.2 g of 5 mass % palladium/activated carbon powder (E1010/W manufactured by Evonik Industries), and 0.12 g of acetic acid were placed and mixed in the same autoclave as that of Example 1. The pH of the mixture was measured by using a pH test paper strip, manufactured by Toyo Roshi, and found to be 6. The atmosphere in the reactor was replaced with hydrogen and pressurized to 0.5 MPa, and the temperature in the reactor was raised to 180° C. Subsequently, the hydrogen pressure was raised to 9.8 MPa. The mixture was allowed to react for 3 hours. Hydrogen was added during the reaction so as to keep the pressure at 9.8 MPa. Gas chromatography analysis of the reaction mixture after the reaction revealed that the conversion rate of HF was 100% and the yield of THF was 99%.

Example 4

60 g of HF, 1.2 g of 5 mass % palladium/activated carbon powder (E1010/W manufactured by Evonik Industries), and 1.8 g of activated earth (Galleon Earth NV manufactured by Mizusawa Industrial Chemicals, Ltd.) were placed and mixed in the same autoclave as that of Example 1. The pH of the mixture was measured by using a pH test paper strip, manufactured by Toyo Roshi, and found to be 6. The atmosphere in the reactor was replaced with hydrogen and pressurized to 0.5 MPa, and the temperature in the reactor was raised to 140° C. Subsequently, the hydrogen pressure was raised to 1.8 MPa. The mixture was allowed to react for 4 hours. Hydrogen was added during the reaction so as to keep the pressure at 1.8 MPa. Gas chromatography analysis of the reaction mixture after the reaction revealed that the conversion rate of HF was 100% and the yield of THF was 92%.

Example 5

60 g of HF and 1.2 g of 5 mass % palladium/activated carbon powder (E1010/W manufactured by Evonik Industries) were placed and mixed in the same autoclave as that of Example 1. The pH of the mixture was measured by using a pH test paper strip, manufactured by Toyo Roshi, and found to be 7. The atmosphere in the reactor was replaced with hydrogen and pressurized to 0.5 MPa, and the temperature in the reactor was raised to 180° C. Subsequently, the hydrogen pressure was raised to 9.8 MPa. The mixture was allowed to react for 3 hours. Hydrogen was added during the reaction so as to keep the pressure at 9.8 MPa. Gas chromatography analysis of the reaction mixture after the reaction revealed that the conversion rate of HF was 100% and the yield of THF was 90%.

Example 6

60 g of 2-hydroxy-4-methyltetrahydropyran (MHP), 3.0 g of 5 mass % palladium/activated carbon powder (E1010/W manufactured by Evonik Industries), and 3.0 g of sodium hydrogen sulfate monohydrate were placed and mixed in the same autoclave as that of Example 1. The pH of the mixture was measured by using a pH test paper strip, manufactured by Toyo Roshi, and found to be 6. The atmosphere in the reactor was replaced with hydrogen and pressurized to 0.5 MPa, and the temperature in the reactor was raised to 100° C. Subsequently, the hydrogen pressure was raised to 0.8 MPa. The mixture was allowed to react for 6 hours. Hydrogen was added during the reaction so as to keep the pressure at 0.8 MPa. Gas chromatography analysis of the reaction mixture after the reaction revealed that the conversion rate of MHP was 98% and the yield of 4-methyltetrahydropyran (MTHP) was 97%.

Example 7

60 g of MHP, 1.2 g of 5 mass % palladium/activated carbon powder (E1010/W manufactured by Evonik Industries), and 0.6 g of 85% phosphoric acid were placed and mixed in the same autoclave as that of Example 1. The pH of the mixture was measured by using a pH test paper strip, manufactured by Toyo Roshi., and found to be 4. The atmosphere in the reactor was replaced with hydrogen and pressurized to 0.2 MPa, and the temperature in the reactor was raised to 100° C. Subsequently, the hydrogen pressure was raised to 0.5 MPa. The mixture was allowed to react for 10 hours. Hydrogen was added during the reaction so as to keep the pressure at 0.5 MPa. Gas chromatography analysis of the reaction mixture after the reaction revealed that the conversion rate of MHP was 99% and the yield of MTHP was 99%.

Example 8

60 g of HF, 1.2 g of 5 mass % palladium/activated carbon powder (E1010/W manufactured by Evonik Industries), and 1.2 g of p-toluenesulfonic acid monohydrate were placed and mixed in the same autoclave as that of Example 1. The pH of the mixture was measured by using a pH test paper strip, manufactured by Toyo Roshi, and found to be 1. The atmosphere in the reactor was replaced with hydrogen and pressurized to 0.5 MPa, and the temperature in the reactor was raised to 120° C. Subsequently, the hydrogen pressure was raised to 1.8 MPa. The mixture was allowed to react for 1 hour. Hydrogen was added during the reaction so as to keep the pressure at 1.8 MPa. Gas chromatography analysis of the reaction mixture after the reaction revealed that the conversion rate of HF was 100% and the yield of THF was 79%.

Example 9

60 g of HF, 1.2 g of 5 mass % palladium/activated carbon powder (E101/W manufactured by Evonik Industries), and 1.2 g of oxalic acid were placed and mixed in the same autoclave as that of Example 1. The pH of the mixture was measured by using a pH test paper strip, manufactured by Toyo Roshi, and found to be 2. The atmosphere in the reactor was replaced with hydrogen and pressurized to 0.5 MPa, and the temperature in the reactor was raised to 120° C. Subsequently, the hydrogen pressure was raised to 1.8 MPa. The mixture was allowed to react for 6 hours. Hydrogen was added during the reaction so as to keep the pressure at 1.8 MPa. Gas chromatography analysis of the reaction mixture after the reaction revealed that the conversion rate of HF was 84% and the yield of THF was 71%.

The invention claimed is:

1. A method for producing a cyclic ether represented by the following formula (2), comprising:
reacting in a reaction mixture a 2-hydroxy cyclic ether, represented by the following formula (1), with hydrogen in the presence of a catalyst and an acid,
wherein the catalyst comprises at least one element from groups 8 to 10 of the periodic table selected from the group consisting of cobalt, nickel, ruthenium, rhodium, iridium, palladium, and platinum, and the acid is at least one selected from the group consisting of an inorganic acid, a sulfonic acid, a carboxylic acid, a heteropoly acid, a solid acid, an acidic ion exchange resin, and a peracid, or a salt thereof:

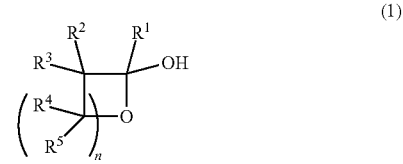

wherein n is an integer in the range of 1 to 7, and $R^1$ to $R^5$ each independently represent a hydrogen atom, an aliphatic hydrocarbon group having 1 to 4 carbon atoms or an aromatic hydrocarbon group having 6 to 12 carbon atoms, and when $R^4$ and $R^5$ exist plurals, they may differ from each other;

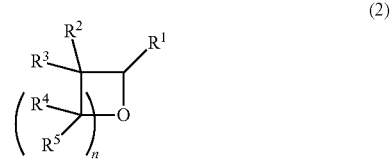

wherein the symbols have the above-defined meanings.

2. The method according to claim 1, wherein the reaction is carried out under the condition that the pH of the reaction mixture falls within the range of 3 to 7.

3. The method according to claim 1, wherein the acid is at least one selected from the group consisting of acetic acid, phosphoric acid, sulfuric acid, hydrochloric acid, nitric acid, a heteropoly acid, and a peracid, or a salt thereof, and wherein the acid exists in the reaction mixture in an amount of 0.001 to 10% by mass based on the total mass of the reaction mixture.

4. The method according to claim 1, wherein the element from groups 8 to 10 of the periodic table is at least one element selected from the group consisting of nickel, ruthenium, rhodium, palladium, and platinum.

5. The method according to claim 1, wherein the catalyst is a supported catalyst.

6. The method according to claim 1, wherein $R^1$ is a hydrogen atom.

7. The method according to claim 1, wherein n is 2 or 3.

8. The method according to claim 1, wherein the element from groups 8 to 10 of the periodic table is at least one element selected from the group consisting of nickel, rhodium, palladium, and platinum.

9. The method according to claim 1, wherein the catalyst is a supported catalyst comprising the at least one element from groups 8 to 10 of the periodic table supported on a carrier selected from the group consisting of activated carbon, silica, alumina, titania, and zeolite.

10. The method according to claim 9, wherein the supported catalyst is palladium-supported activated carbon, platinum-supported activated carbon, palladium-supported silica, palladium-supported alumina, or palladium-supported titania.

11. The method according to claim 1, wherein the catalyst is used in an amount of 0.0001 to 10% by mass, based on a mass of the 2-hydroxy cyclic ether represented by formula (1).

12. The method according to claim 1, wherein the reaction is carried out at a reaction temperature in the range of 40 to 250° C.

13. The method according to claim 1, wherein the reaction is carried out at a reaction pressure in the range of 1 kPa to 20 MPa.

* * * * *